US012643908B2

(12) United States Patent
Gorbachev et al.

(10) Patent No.: US 12,643,908 B2
(45) Date of Patent: Jun. 2, 2026

(54) PROCESS FOR THE SYNTHESIS OF NOROXYMORPHONE FROM MORPHINE

(71) Applicant: NAVIN SAXENA RESEARCH & TECHNOLOGY PVT. LTD., Mumbai (IN)

(72) Inventors: Dmitry Gorbachev, Nottingham (GB); Hon Wai Lam, Nottingham (GB); Aakarsh Saxena, Mumbai (IN); Navin Satyapal Saxena, Mumbai (GB)

(73) Assignee: NAVIN SAXENA RESEARCH & TECHNOLOGY PVT. LTD., Mumbai (IN)

( * ) Notice: Subject to any disclaimer, the term of this patent is extended or adjusted under 35 U.S.C. 154(b) by 435 days.

(21) Appl. No.: 18/342,381

(22) Filed: Jun. 27, 2023

(65) Prior Publication Data

US 2023/0357257 A1 Nov. 9, 2023

Related U.S. Application Data

(63) Continuation of application No. PCT/IN2021/050262, filed on Mar. 15, 2021.

(51) Int. Cl.
*C07D 489/08* (2006.01)

(52) U.S. Cl.
CPC .................................. *C07D 489/08* (2013.01)

(58) Field of Classification Search
CPC ............................ C07D 489/08; C07D 489/02
USPC ...................................................... 546/45, 44
See application file for complete search history.

(56) References Cited

U.S. PATENT DOCUMENTS

| | | | |
|---|---|---|---|
| 4,795,813 | A | 1/1989 | Schwartz |
| 5,112,975 | A | 5/1992 | Wallace |
| 9,546,177 | B2 | 1/2017 | Weber |

FOREIGN PATENT DOCUMENTS

| | | | |
|---|---|---|---|
| EP | 0158476 | A1 | 10/1985 |
| WO | 2015/011131 | A | 1/2019 |

OTHER PUBLICATIONS

Ninan, Tetrahedron vol. 48, Issue 32, 1992, pp. 6709-6716 (Abstract).
International Search Report and Written Opinion for PCT/IN2021/050262 mailed on Aug. 19, 2021.
European Medicines Agency (EMA) ICH guideline Q3C (R6) on impurities: guideline for residual solvents (2019).
Yujiro Hayashi, "Pot Economy and One-Pot Synthesis," Chem. Sci. 2016, 7, 866-880.

*Primary Examiner* — Charanjit Aulakh
(74) *Attorney, Agent, or Firm* — Kramer & Amado, P.C.

(57) ABSTRACT

The present invention relates to a novel, efficient, pot- and atom-economical, and industrially applicable process for converting morphine to noroxymorphone using reagents and solvents of lesser toxicity and lower cost with respect to those used in the prior art.

19 Claims, No Drawings

PROCESS FOR THE SYNTHESIS OF NOROXYMORPHONE FROM MORPHINE

FIELD OF THE INVENTION

The present invention relates to a novel, efficient, pot- and atom-economical, and industrially applicable process for converting morphine to noroxymorphone using reagents and solvents of lesser toxicity and lower cost with respect to those used in the prior art.

BACKGROUND OF THE INVENTION

The morphinan compounds are a group of structurally related alkaloids that can act as opiate receptor agonists or opiate receptor antagonists. Mu-opiate receptor agonists such as morphine, hydromorphone, codeine, hydrocodone, dihydromorphine, dihydrocodeine, oxycodone, hydromorphone, and oxymorphone are useful as analgesics for pain relief. However, compounds such as naloxone, naltrexone, and nalmefene are mu-opiate receptor antagonists useful for the treatment of substance abuse or to reverse the effects of mu-opiate agonists. Other examples of semi-synthetic derivatives of naturally occurring opium-based alkaloids that exhibit useful medicinal activity include methyl naltrexone bromide, naloxegol, nalbuphine, nalfurafine, etc. The broad family of mu-opiate receptor antagonists are commonly referred to as “nal-derivatives” or “nal-compounds”. Examples of various medicinally relevant nal-derivatives are shown below.

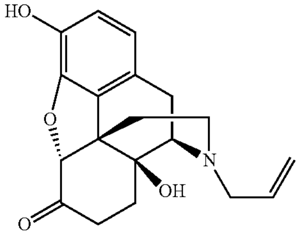

naloxone

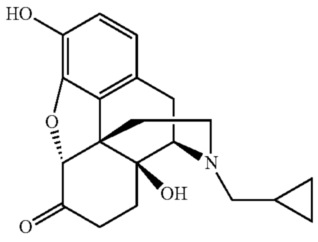

naltrexone

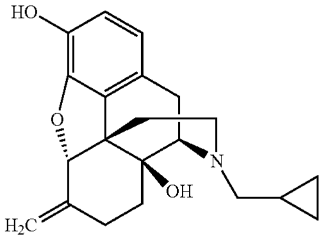

nalmefene

-continued

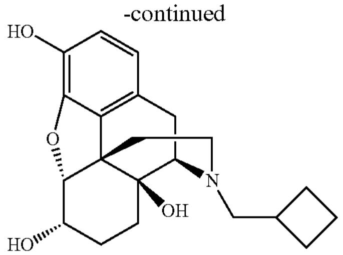

nalbuphine

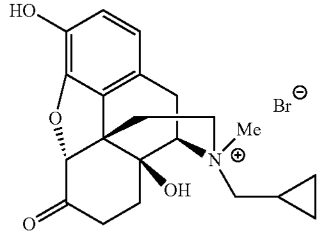

methyl naltrexone bromide

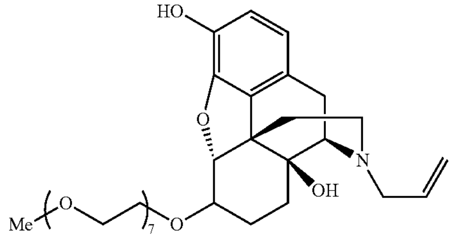

naloxegol

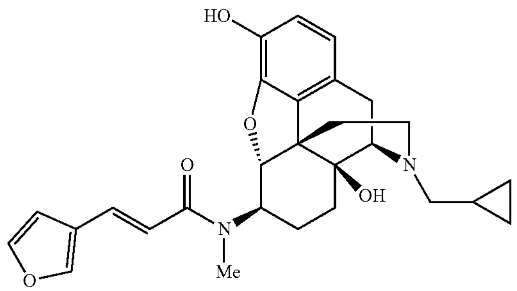

nalfurafine

The syntheses of these medicinally relevant compounds utilize noroxymorphone (compound I) as a common intermediate for late-stage diversification leading to the preparation of the aforementioned nal-derivatives. The diverse range of active pharmaceutical ingredients (APIs) that can be prepared through noroxymorphone makes the efficient synthesis of this intermediate of particular interest. Presently, the more common routes of synthesis of noroxymorphone employ naturally occurring alkaloids such as thebaine and oripavine; however, these starting materials pose several limitations. For example, thebaine and oripavine are found and extracted in scarce quantities from the poppy plant (botanical name: *Papaver somniferum*). Relative to thebaine and oripavine, the content of morphine in the poppy plant is significantly higher thus making morphine more abundantly available and at an appreciably reduced cost.

For these reasons, an efficient and industrially applicable synthesis of noroxymorphone from morphine would be highly desirable. Synthesis of noroxymorphone (compound I) from oripavine and thebaine is shown in Scheme 1.

Scheme 1

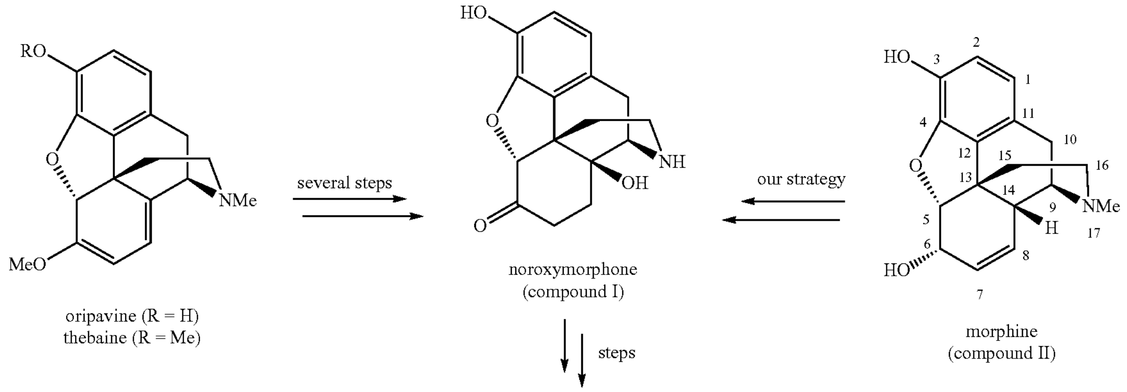

oripavine (R = H)
thebaine (R = Me)

noroxymorphone
(compound I)

morphine
(compound II)

various nal-derivatives

B. T. Weber and L. Hochstrasser in the U.S. Pat. No. 9,546,177 (EP 3 024 835) disclose processes for the conversion of morphine to noroxymorphone. The route of synthesis is essentially similar to a previously published patent U.S. Pat. No. 5,112,975 (EP 0 158476) reported by R. A. Wallace. The 6-step route of synthesis in both patents is illustrated in Scheme 2. Besides certain trivial and obvious process-related changes, the two key points of difference between the two patents happens to be the set of conditions used for a) the oxidation of allylic alcohol of formula (A) to the corresponding enone of formula (B) and, b) the conversion of the dienol acetate of formula (C) to the corresponding 14-hydroxyenone of formula (D), as shown in Scheme 2.

Scheme 2

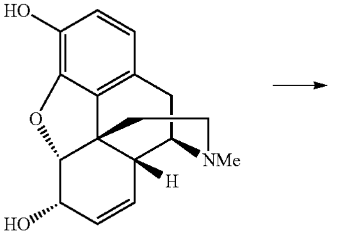

morphine (II)

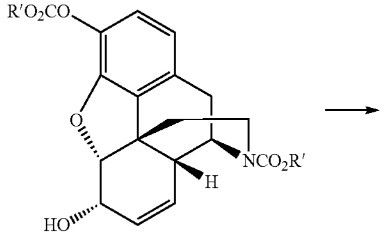

(A)

-continued

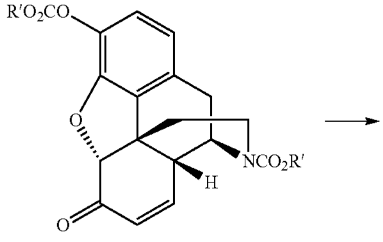

(B)

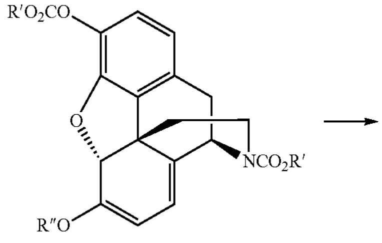

(C)

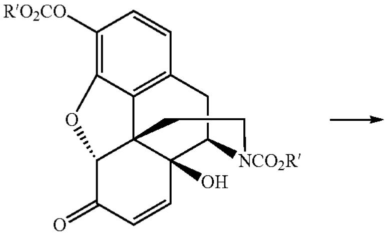

(D)

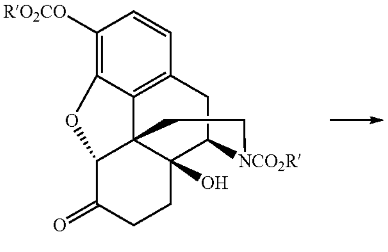

(E)

-continued

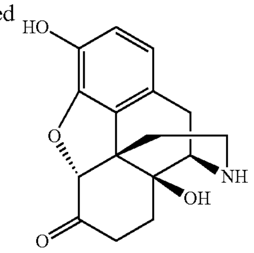

noroxymorphone (I)
[Step count = 6]

Upon careful inspection of both patents several major drawbacks and limitations were identified which make these processes industrially non-viable. For example:

The first step is performed using either chloroform (U.S. Pat. No. 5,112,975) or dichloromethane (U.S. Pat. No. 9,546,177) as a solvent. According to the European Medicines Agency's (EMA) Q3C(R6) Guideline for Residual Solvents, chloroform and dichloromethane are classified as 'Class 2' solvents. According to the EMA, Class 2 solvents " . . . should be limited in pharmaceutical products because of their inherent toxicity." Similarly, according to the EMA, Class 3 solvents " . . . may be regarded as less toxic and of lower risk to human health." Therefore, the use of a Class 3 solvent would be highly desirable.

The second step is performed using Swern oxidation conditions (U.S. Pat. No. 9,546,177). The Swern oxidation is deployed routinely for the oxidation of alcohols to ketones in small-scale academic endeavours owing to the use of less-toxic reagents relative to alternative metal-mediated oxidation reactions, and high functional group tolerance; however, this methodology necessitates pre-cooled reaction conditions of temperatures reaching as low as −80° C. Attaining and maintaining such extremely low reaction temperatures over an extended duration of time on an industrial scale is impractical. In the U.S. Pat. No. 9,546,177, the inventors acknowledge this major drawback and attempt to resolve it by conducting the Swern oxidation at room temperature only to observe the generation of large quantities of an unwanted side-impurity, which severely detracts from the merits of the process. In U.S. Pat. No. 5,112,975, the second step is performed using Jones' reagent, which is a highly toxic chromium-based oxidizing agent. This poses serious environmental, health, and safety concerns. Alternatively, the oxidation may be performed using manganese dioxide as the oxidizing agent as reported in FR 2,515,184 (U.S. Pat. No. 4,795,813) and in *Tetrahedron* 1992, 48(11), 6709-6716. Unfortunately, super-stoichiometric quantities of manganese dioxide are required for this oxidation to proceed making this methodology atom-uneconomical and leading to the generation of a large excess of inorganic waste. The solvent used for the manganese dioxide-mediated oxidation of compound of formula (A) is chloroform, which is a toxic solvent. Therefore, the oxidation of compound of formula (A) using less-toxic reagents and reaction conditions that are more industrially applicable is highly desirable.

In all prior reports the second and third steps shown in Scheme 2 are performed as distinct steps in separate reaction pots. For an efficient multi-step synthetic process, pot-economy is of vital importance as it helps to streamline the entire manufacturing process by telescoping multiple transformations into a single-pot reaction, thereby increasing overall process efficiency. Therefore, a single-pot conversion of compound of formula (A) to compound of formula (C), thus precluding the need to isolate compound of formula (B) would be highly desirable.

The fourth step is performed using either m-chloroperbenzoic acid (U.S. Pat. No. 5,112,975) or performic acid (U.S. Pat. Nos. 9,546,177 and 5,112,975) as the oxidizing agent. m-Chloroperbenzoic acid (mCPBA) is both unstable and expensive, thus not ideal. Additionally, the molecular weight (M.W.) of mCPBA is 172.57 g/mol. During the conversion of compound of formula (C) to compound of formula (D) as shown in Scheme 2, a hydroxyl group (M.W.$\approx$17 g/mol) is installed, implying a mass transfer of only 9.85% of mCPBA's molecular weight. This makes mCPBA a highly atom-uneconomical reagent. Atom-economy is of a vital importance as it helps to reduce the generation of waste by-products in reactions, thereby making the overall process safer and greener. Therefore, the use of a more atom-economical peracid to effect the above transformation is desirable. Relative to mCPBA, performic acid (M.W.=62.02 g/mol) is significantly cheaper and more atom-economical (mass transfer of 27% of performic acid's molecular weight); however, it too is highly unstable. While attempting to reproduce the procedure reported in U.S. Pat. No. 9,546,177 for the conversion of compound of formula (C) to compound of formula (D) as shown in Scheme 2 using pre-formed performic acid, we observed the generation of significant quantities of undesired side-products including 7,8-epoxide derivatives of the dienol acylate. This observation is consistent with the findings of U.S. Pat. No. 9,546,177. Therefore, the conversion of compound of formula (C) to compound of formula (D) while minimizing the formation of undesired impurities is highly desirable.

In prior reports, the fourth and fifth steps shown in Scheme 2 are performed as distinct steps in separate reaction pots. For instance, after the peracid-mediated oxidation of compound of formula (C) to compound of formula (D) is completed, the reaction mixture is transferred to a hydrogenation autoclave reaction pot. As mentioned previously, by optimizing the pot-economy of a process and enhancing the ability to perform multiple transformations as a single-pot process can have a profound impact on the overall efficiency of a multi-step process. Therefore, a single-pot conversion of compound of formula (C) to compound of formula (E) would be highly desirable.

The reported overall yield in U.S. Pat. No. 9,546,177 is 37%, whereas the reported overall yield in U.S. Pat. No. 5,112,975 is about 60%. Therefore, a higher-yielding process is desirable.

The reported purity by assay of noroxymorphone in U.S. Pat. No. 5,112,975 is 90% only, whereas the reported purity by HPLC of noroxymorphone in U.S. Pat. No. 9,546,177 is 94% only. Hence, a process leading to the formation of noroxymorphone of superior quality is also desirable.

The conversion of morphine to noroxymorphone in both U.S. Pat. No. 5,112,975 and in U.S. Pat. No. 9,546,177 are reported as six-pot processes, as shown in Scheme 2. Hence, a process with better pot-economy is highly desirable. In our analysis, we have adopted the generally-accepted definition of 'pot-economy' that is provided in *Chem. Sci.* 2016, 7, 866-880 wherein it is stated that " . . . a one-pot synthesis is defined as a strategy to improve the efficiency of a chemical reaction, whereby a reactant is subjected to successive chemical reactions in just one [single] reactor." For the purpose of the present invention, the terms 'pot', 'vessel', 'flask', 'mixer', 'reactor', 'static/bulk reactor', 'continuous flow reactor', 'microwave reactor', and other such similar terms are considered equivalent to each other such that they all are devices in which a chemical transformation may occur. We have also adopted the generally-accepted definition of 'atom-economy' provided in the same report which states " . . . that synthetic methods should be designed to maximize the incorporation of all materials used in the process into the final product (ACS Green Chemistry Principles #2)."

Therefore, there remains a need in the art for an efficient, pot- and atom-economical, and industrially applicable process for converting morphine of formula (II) to noroxymorphone of formula (I) using environmentally-benign reagents with lesser toxicity and at lower cost.

SUMMARY OF THE INVENTION

The current invention provides an improved process with the purpose of addressing the drawbacks and limitations found in the prior arts as highlighted in the above section. Accordingly, the present invention relates to an improved process for producing noroxymorphone from morphine (Scheme 3) comprising of the following steps:

1. reacting morphine of formula (II) to obtain a compound of formula (III), wherein $R^1$ and $R^2$ independently are a substituted or unsubstituted alkyl group with 1 to 20 carbon atoms, or a substituted or unsubstituted aryl group, or a substituted or unsubstituted alkylaryl group with 1 to 20 carbon atoms, or a substituted or unsubstituted alkenyl group having 2 to 20 carbon atoms, or a substituted or unsubstituted alkoxycarbonyl group with 1 to 20 carbon atoms in the alkyl residue, or a substituted or unsubstituted aryloxycarbonyl group or a substituted or unsubstituted arylalkoxycarbonyl group with 1 to 20 carbon atoms in the alkyl residue, or a cyanide group, or a silyl group of formula $Si(R^4)_3$, wherein the groups $R^4$ can be the same or different and are each selected from substituted or unsubstituted alkyl groups having 1 to 6 carbon atoms and substituted or unsubstituted aryl groups, respectively;

2a. oxidizing the compound of formula (III) with an oxidizing agent to obtain a compound of formula (IV), respectively;

2b. acylating the compound of formula (IV) with an acylation agent to obtain a compound of formula (V), wherein $R^1$ and $R^2$ independently are a substituted or unsubstituted alkyl group with 1 to 20 carbon atoms, or a substituted or unsubstituted aryl group, or a substituted or unsubstituted alkylaryl group with 1 to 20 carbon atoms, or a substituted or unsubstituted alkenyl group having 2 to 20 carbon atoms, or a substituted or unsubstituted alkoxycarbonyl group with 1 to 20 carbon atoms in the alkyl residue, or a substituted or unsubstituted aryloxycarbonyl group or a substituted or unsubstituted arylalkoxycarbonyl group with 1 to 20 carbon atoms in the alkyl residue, or a cyanide group, or a silyl group of formula $Si(R^4)_3$, wherein the groups $R^4$ can be the same or different and are each selected from substituted or unsubstituted alkyl groups having 1 to 6 carbon atoms and substituted or unsubstituted aryl groups, respectively, and wherein $R^3$ is a substituted or unsubstituted alkylcarbonyl group having 1 to 20 carbon atoms in the alkyl residue, or a substituted or unsubstituted arylalkylcarbonyl group having 1 to 20 carbon atoms in the alkyl residue, or a substituted or unsubstituted arylcarbonyl group, or a substituted or unsubstituted alkenylcarbonyl group having 2 to 20 carbon atoms, respectively;

3a. subjecting the compound of formula (V) to peroxy oxidation to obtain a compound of formula (VI), respectively;

3b. reducing the compound of formula (VI) to obtain a compound of formula (VII), respectively; and 4. hydrolyzing the compound of formula (VII) to obtain noroxymorphone of formula (I);

wherein step 2a is conducted using Albright-Goldman oxidation conditions, wherein step 2a & step 2b may be combined into a one-pot single-step transformation, and, wherein step 3a & step 3b may be combined into a one-pot single-step transformation.

The novel, pot-economical process for preparing noroxymorphone from morphine according to the present invention is shown in Scheme 3 below.

Scheme 3

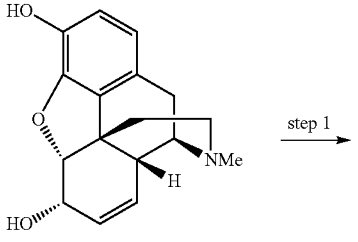

morphine (II)

-continued

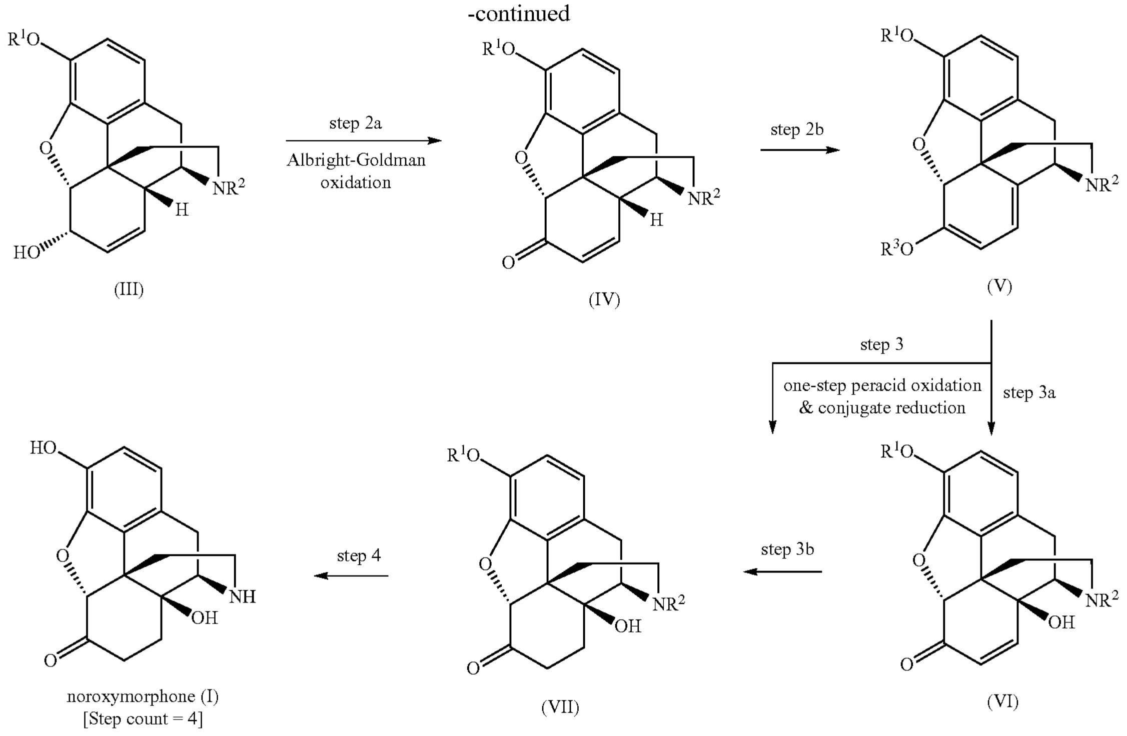

The present invention additionally describes the use of non-toxic non-halogenated polar organic solvents for the conversion of morphine of formula (II) to a compound of formula (III), as shown in step 1 of Scheme 3. In particular, Class 3 solvents, as defined by the ICH Q3C(R6) Guideline for Residual Solvents, have been successfully used for the first time to affect this transformation.

The present invention also describes, as shown in step 2 of Scheme 3, the direct and efficient one-pot conversion of the allylic alcohol of formula (III) to the corresponding dienol acylate of formula (V) via the in-situ formation of compound of formula (IV) under mild, industrially applicable conditions.

The present invention still further describes, as shown in step 3 of Scheme 3, the direct and efficient one-pot conversion of compound of formula (V) to the compound of formula (VII) via the in-situ formation of compound of formula (VI) under mild, industrially applicable conditions.

Further preferred embodiments of the present invention are defined in the dependent claims.

DETAILED DESCRIPTION OF THE INVENTION

The invention will now be described in detail in connection with certain preferred and optional embodiments, so that various aspects thereof may be more fully understood and appreciated.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. To provide a more concise description, some of the quantitative expressions herein are recited as a range from about amount X to about amount Y. It is understood that where a range is recited, the range is not limited to the recited upper and lower bounds, but rather includes the full range from about amount X through about amount Y, or any amount or range therein.

Accordingly, in one aspect, the present invention relates to a process for converting morphine of formula (II) to noroxymorphone of formula (I), which is characterized by the steps as illustrated in Scheme 3.

The starting material, morphine, used in the present invention was procured from Spain.

In compounds of formula (III), (IV), (V), (VI), and (VII) shown in Scheme 3, $R^1$ and $R^2$ are defined as in the above section, wherein, $R^1$ is preferably selected from an ethoxycarbonyl group, or an acetyl group, or a methyl group, or a silyl group of formula $Si(R^4)_3$, wherein the groups $R^4$ can be the same or different and are each selected from substituted or unsubstituted alkyl groups having 1 to 6 carbon atoms and $R^2$ is preferably selected from an ethoxycarbonyl group, or a cyanide group. However, in a preferred embodiment, wherein $R^1$ and $R^2$ are preferably an ethoxycarbonyl group. In compound of formula (V) shown in Scheme 3, $R^1$ and $R^2$ are preferably an ethoxycarbonyl group, and $R^3$ is defined as in the above section, wherein $R^3$ preferably is a methylcarbonyl, also commonly referred to as an acetyl group. The reaction steps presented henceforth correspond to those enumerated in Scheme 3.

Although, the description of the invention, including conditions and parameters for Steps 1-4 set forth below of the process for preparing noroxymorphone from morphine, is given with principal reference to such steps and associated compounds produced therein for the case where Step 1 is carried out using an ethylhaloformate ester (e.g., ethylchloroformate) and the acyl group ($R^3$) is acetyl by way of illustration; however, it is to be construed that other $R^1$, $R^2$ and $R^3$ groups may be substituted in whole or in part for the ethoxycarbonyl and acetyl groups, respectively, to obtain noroxymorphone from morphine.

Step 1:

Accordingly, in Step 1 of the present process for preparing noroxymorphone of formula (I) from morphine of formula (II), the initial step is conversion of morphine of formula (II) to compound of formula (III) as shown in Scheme 3, thereby introducing, preferably, a carbonate group at the C-3 hydroxyl position and a carbamate group at the N-17 amino position. The reaction proceeds by contacting morphine with, for example, a haloformate ester of the formula X—C(═O)OR$^5$ where X is a halogen, preferably bromine or chlorine or more preferably chlorine, whereby the haloformate ester is a chloroformate, and $R^5$ is a substituted or unsubstituted alkyl group with 1 to 20 carbon atoms, or a substituted or unsubstituted aryl group, or a substituted or unsubstituted alkylaryl group with 1 to 20 carbon atoms, or a substituted or unsubstituted alkenyl group having 2 to 20 carbon atoms. Illustrative $R^5$ groups within the above definition are methyl, ethyl, propyl, heptyl, 1,1,1-trichloroethyl, vinyl, butenyl, phenyl, benzyl, carbobenzyl, and naphthyl groups. Preferably, $R^5$ is an ethyl group and therefore, ethyl chloroformate is the preferred haloformate ester.

The reaction is preferably carried out under an inert atmosphere in the presence of an inert non-toxic organic solvent in which the reactants can be dissolved or dispersed under the reaction conditions employed to form a solution, dispersion, suspension or other reaction mixture. As used herein, the modifying term "inert" means that the substance referred to in connection with an associated reaction is at least substantially nonreactive with the reactants and desired product or products.

The haloformate ester is preferably added slowly to a solution or other mixture of morphine in the organic solvent employed, with stirring. The organic solvent may be selected from, for example, an arene, ketone, ester, halogenated alkane, halogenated arene or a mixture of two or more of such organic solvents. In an embodiment, acetone, ethyl acetate or their mixture is preferred as the solvents. In another embodiment, ethyl acetate is more preferred as the solvent.

The reaction is preferably promoted by a weak base which may be, selected from bicarbonates such as potassium bicarbonate, and sodium bicarbonate; carbonates such as sodium carbonate, potassium carbonate or a mixture of two or more of such weak bases. In a preferred embodiment, sodium bicarbonate is used as a weak base.

The reaction in Step 1 can be carried out by employing per mole of morphine: about 5-15 moles of the haloformate ester such as an alkyl, alkenyl, arylalkyl or aryl bromoformate or chloroformate, preferably about 9.0 moles of ethyl chloroformate; about 10-25 moles of a weak base, preferably about 15 moles of sodium bicarbonate; and about 0.1-100 litres of an organic solvent, preferably about 1-10 litres of ethyl acetate or acetone or their combination, and more preferably about 3 litres when ethyl acetate or acetone or their combination is used as the organic solvent. The reaction may suitably be effected at, for example atmospheric pressure and a temperature of about 30° C.-100° C., while about 35° C.-45° C. is preferred when acetone is used as the organic solvent, and about 70° C.-80° C. is preferred when ethyl acetate is used as the organic solvent. The inert atmosphere is preferably nitrogen.

Preferably, the reaction of step 1 is substantially anhydrous by using the reaction components substantially anhydrous, i.e., the mixture does not contain more than 10% water, and more preferably not more than 5% water.

After completion of the reaction, the product of formula (III) is isolated by cooling the reaction mixture to room temperature (about 30° C.), filtering the reaction mixture, then concentrating and drying the obtained filtrate.

By employing ethyl acetate as the reaction solvent, which is a less toxic and environmentally-benign solvent, Step 1 of the present process has been significantly improved over previous reports that use highly toxic and environmentally-harmful halogenated solvents such as chloroform and dichloromethane.

Step 2a:

In the next step of the present process for preparing noroxymorphone from morphine, compound of formula (III) is converted to compound of formula (IV) as shown in Scheme 3, thereby converting the allylic alcohol moiety in compound of formula (III) to the corresponding enone moiety in compound of formula (IV) using Albright-Goldman oxidation conditions. The conversion of compound of formula (III) to the compound of formula (IV) using Albright-Goldman oxidation conditions has, to the best of our knowledge, not been reported in the literature previously. In the Albright-Goldman oxidation, as understood within the scope of this invention, generally a primary or secondary alcohol is oxidized under mild conditions to the corresponding aldehyde or ketone respectively by contacting the alcohol with an acyclic or cyclic organic acid anhydride and a dialkyl sulfoxide.

In the present instance, the reaction proceeds by contacting compound of formula (III) with an acyclic or cyclic organic acid anhydride and a dialkyl sulfoxide at room temperature with stirring or at an elevated temperature with stirring in order to reduce the reaction time. The reaction is preferably carried out in an inert atmosphere under anhydrous conditions. The acid anhydride serves as a reactant as well as the organic solvent in which the remaining reactants can be dissolved or dispersed under the reaction conditions employed to form a solution, dispersion, suspension or other reaction mixture.

The acyclic organic acid anhydride employed in the reaction of Step 2a is of the formula $(R^3)_2O$ where $R^3$ is as defined above. Illustrative acyclic organic acid anhydrides within the above definition are acetic anhydride, propionic anhydride, butanoic anhydride, pentanoic anhydride, hexanoic anhydride, isobutyric anhydride, isovaleric anhydride, acrylic anhydride, methacrylic anhydride, angelic anhydride, crotonic anhydride, benzoic anhydride, and substituted benzoic anhydrides. However, in one preferred embodiment, acetic anhydride is the acyclic organic acid anhydride. In another preferred embodiment, benzoic anhydride is the acyclic organic acid anhydride.

The cyclic organic acid anhydride employed in the reaction of Step 2a is of the formula (VIII) shown below, wherein $R^6$ is a substituted or unsubstituted alkyl group with 2 to 20 carbon atoms in the alkyl residue, or a substituted or unsubstituted aryl group, or a substituted or unsubstituted alkenyl group having 2 carbon atoms. Illustrative cyclic organic acid anhydrides within the above definition are succinic anhydride, maleic anhydride, glutaric anhydride, adipic anhydride, 3-methylglutaric anhydride, 3,3-dimethylglutaric anhydride, hexafluoroglutaric anhydride, phthalic anhydride, homophthalic anhydride, etc. However, in one preferred embodiment, glutaric anhydride is the cyclic organic acid anhydride.

(VIII)

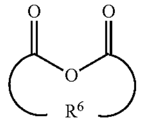

Dimethyl sulfoxide (DMSO) is the preferred dialkyl sulfoxide.

Suitable oxidation conditions for the reaction in Step 2a include the addition or presence of, per mole of compound of formula (III): about 1 to 1000 moles of the organic acid anhydride, preferably about 10 to 50 moles of acetic anhydride, and more preferably about 25 moles of acetic anhydride; about 1 to 100 moles of DMSO, preferably about 1 to 20 moles of DMSO, and more preferably about 10 moles of DMSO. The reaction may suitably be effected at, for example, atmospheric pressure and a temperature of about 0° C.-120° C., while about 70° C.-85° C. is preferred. The inert atmosphere is preferably nitrogen. Anhydrous conditions substantially as described in Step 1 are preferred.

At the conclusion of the reaction, which may be completed within, for example, about four hours, the product of formula (IV) may be recovered from the reaction mixture in any suitable manner. Preferably, following completion of the reaction, the reaction mixture is cooled to room temperature (about 30° C.), and quenched using any suitable quenching procedure. Preferably, a saturated aqueous solution of sodium bicarbonate is added to the reaction mixture to aid in quenching, followed by extraction of the compound of formula (IV) into an organic solvent and evaporating at least a substantial portion of the organic solvent from the combination to give the compound of formula (IV) as a solid. The organic solvent used for extraction may be, for example, an arene, ketone, ether, ester, halogenated alkane or halogenated arene capable of preferentially dissolving compound of formula (IV) and thereafter evaporating the extraction solvent to yield the desired product of formula (IV). Cyclopentylmethyl ether is preferred for use as the extraction solvent.

Step 2b:

In the subsequent step of the present process for preparing noroxymorphone from morphine, acylation of the compound of formula (IV) is effected by reactively contacting that compound with an acylating agent which is an acid anhydride of the formula $(R^3)_2O$ or an acyl halide of the formula $R^3X$ where $R^3$ is as defined above and X is a halogen, whereby the dienol acylate compound of formula (V) is prepared. Preferably, X is bromide or more preferably chloride, and $R^3$ is acetyl.

The acetylation or other acylation reaction is preferably carried out under an inert atmosphere in the presence of a catalytic acid (hereinafter referred to as an "acid catalyst") or more preferably in the presence of a catalytic base (hereinafter referred to as a "base catalyst").

Suitable conditions for the reaction in step 2b of Scheme 3 include the addition or presence of, per mole of the compound of formula (IV): about 0.01-50 moles of base (i.e., base catalyst) and about 1-100 moles of acylating agent. The reaction may suitably be effected at, for example, atmospheric pressure and a temperature of about 0° C.-120° C., while about 75° C.-85° C. is preferred. The inert atmosphere is preferably nitrogen. Anhydrous conditions substantially as described above for Step 1 are preferred.

Suitable acylating agents include, for example, acetyl chloride and mixed anhydrides of acetic acid. Acetic anhydride is preferred. The base catalyst may be, selected from sodium or potassium acetate, pyridine, triethylamine or mixtures of two or more of the foregoing bases. Triethylamine is generally preferred as the catalyst, especially where acetic anhydride is employed as the preferred acylating agent. Preferably, per mole of the compound of formula (IV), there are employed about 10 moles of preferably anhydrous triethylamine and about 20 moles of acetic anhydride, which also functions as a solvent.

Suitable acid catalysts include, for example, p-toluene sulfonic acid and boron trifluoride etherate. The conditions and parameters set forth above for step 2b are generally applicable for use with the various $R^1$, $R^2$ and $R^3$ groups within the above definitions.

After the completion of the reaction, which may be completed within, 2 to 4 hours, the dienol acylate of formula (V) may be recovered by cooling the reaction mixture to room temperature (about 30° C.), and recovery is effected employing an extraction procedure. Such extraction may be effected using an organic solvent which may be, for example, an arene, ketone, ether, ester, halogenated alkane or halogenated arene capable of preferentially dissolving compound of formula (V) and thereafter evaporating the extract solvent to yield the desired product of formula (V). Cyclopentylmethyl ether is preferred for use as the extraction solvent. Preferably, the cooled reaction mixture is diluted with water and extracted using cyclopentylmethyl ether. The resulting organic solvent extract containing the compound of formula (V) is washed with a saturated aqueous solution of sodium bicarbonate, the resulting organic layer is dried over anhydrous sodium sulfate, followed by evaporation of the organic solvent to yield the desired compound of formula (V) as a solid.

Step 2:

Although it is advantageous to cool the reaction mixture following completion of the reaction as described in Step 2a above and before the extraction procedure as described in Step 2a, such cooling can be satisfactorily omitted. Similarly, recovery of the compound of formula (IV) can be satisfactorily omitted prior to initiation of Step 2b, which can proceed in situ in the reaction mixture of Step 2a.

The one-pot conversion of compound of formula (III) to the compound of formula (V) via the in situ formation of compound of formula (IV) proceeds by contacting compound of formula (III) with an organic acid anhydride and a dialkyl sulfoxide as described above in Step 2a at an elevated temperature with stirring under an inert atmosphere of nitrogen until HPLC analysis detects <5% of the reactant of formula (III) (reaction time of about 4 hours), at which point a base catalyst or an acid catalyst as described above in Step 2b is introduced into the reaction mixture and allowed to stir at an elevated temperature under an inert atmosphere of nitrogen for about 2 further hours. At the conclusion of the reaction, the dienol acylate of formula (V) may be recovered from the reaction mixture in any suitable manner. Preferably, the recovery of compound of formula (V) is effected using the same recovery procedure described in Step 2b above.

Therefore, it has been shown in the present invention that compound of formula (III) may be directly converted to compound of formula (V) in a single-pot transformation via the in-situ formation of compound of formula (IV), thereby making the overall transformation pot- and atom-economical. This transformation is conducted using cheap, less toxic, highly stable reagents and can be performed under reaction parameters (such as reaction temperature and reaction pressure) that can be easily applied on an industrial scale.

Step 3a:

In the next step of the present process for preparing noroxymorphone from morphine, compound of formula (VI) is prepared by contacting the compound of formula (V) with a peroxy oxidation agent for example, performic acid; peracetic acid; monopermaleic acid; trifluoroperacetic acid; trichloroperacetic acid; substituted or unsubstituted perbenzoic acids, wherein the substituent may be, for example, chloro, bromo, iodo, fluoro or nitro. Suitable peracids may be used as aqueous solutions or in pure form.

The peracid may be formed in situ, that is, in the presence of the dienol acylate, by reaction of aqueous hydrogen peroxide with the corresponding acid or corresponding acid anhydride. A concentration of aqueous hydrogen peroxide no less than about 30% (w/w) is preferred. Preferably, the peracid is prepared prior to contacting it with the dienol acylate.

The dienol acylate of formula (V) is reacted with the peroxy oxidation agent under reaction conditions effective for introducing or substituting a hydroxyl group at the C-14 position of the dienol acylate such that the compound of formula (VI) is formed. Preferably, the peroxy oxidation agent in pure form or in the form of an aqueous solution is added to a solution or other mixture containing the dienol acylate in an inert organic solvent, which is substantially nonreactive with the dienol acylate and the peracid. The solvent advantageously is present in a solubilizing amount for each of the dienol acylate and the peracid.

The organic solvent is preferably a polar organic solvent such as for example, acetic acid, dimethylformamide, chloroform, methylene chloride (dichloromethane), methanol, ethanol, 1-propanol, 2-propanol, 1-butanol, acetonitrile, 1,2-dimethoxyethane, n-propyl acetate and mixtures thereof. Acetic acid is preferred, while glacial acetic acid is more preferred.

In addition to the solvent and the dienol acylate, the reaction mixture may include other components. For example, the reaction mixture may include agents effective for inhibiting formation of 7,8-epoxide derivatives of the dienol acylate and other side reaction products. It has been previously reported (U.S. Pat. No. 5,112,975) that the inclusion of an acid catalyst, viz., an acid having pKa in the range of about 0 to about 3 or slightly higher permits preparation of the enone of formula (VI) in higher yield. However, in the present invention it has been observed that the inclusion of an acid catalyst into the reaction mixture had no significant deleterious nor advantageous effect on the reaction outcome. Therefore, an acid catalyst may optionally be added into the reaction mixture as a precautionary inclusion.

The reaction conditions preferably further include effecting the reaction of the dienol acylate with the peroxy oxidation agent in the substantial absence of water, i.e., with water preferably not present in an amount greater than 5 percent by weight based on the weight of the reaction mixture. Such reaction conditions may conveniently be provided by employing anhydrous components for the reaction mixture and conducting the reaction under an inert anhydrous atmosphere, e.g., dry nitrogen. During the formation of the peracid, by contacting aqueous hydrogen peroxide with the corresponding acid or corresponding acid anhydride, a concentration of aqueous hydrogen peroxide no less than about 30% (w/w) is preferred so as to minimize the presence of water in the peracid solution. Besides aqueous hydrogen peroxide, preferably, substantially no water of hydration is present in any of the components of the reaction mixture. Similarly, solvents added in the reaction mixture, for example glacial acetic acid or formic acid, are preferably of a purity no less than 95%, and more preferably of a purity no less than 98%.

The peracid solution is preferably added to the dienol acylate in a continuous dropwise flow rate, and at an average rate of from about 0.01 to about 0.1 gram-equivalent per minute per mole of the dienol acylate. Desirably, a total of at least 1 gram-equivalent of the peracid is added per mole of the dienol acylate. The addition may advantageously be made over a period from about 30 to about 120 minutes, preferably with stirring of the reaction mixture.

The reaction may effectively be conducted at any suitable pressure (preferably about atmospheric pressure) and at any suitable temperature, e.g., about −10° to 100° C., preferably about −5 to 5° C.

The peracid may be added in a total amount of, for example, about 1 to about 10 moles and more preferably at about 5 moles on the same basis. The acid catalyst if employed, may be in an amount of, for example, about 0.01 to 0.5 mole, preferably about 0.5 mole, per mole of the dienol acylate. The solvent may be present in an amount of, for example, about 0.5 to 20 liters, preferably about 5-10 liters, per mole of the dienol acetate.

After the completion of the reaction, the enone of formula (VI) can be conveniently recovered by quenching the reaction mixture with water or preferably an aqueous alkali, for example, an aqueous solution of $NH_4OH$ is preferred. Thereafter, the enone compound can be separated by extraction of the quenched mixture using a water-immiscible organic solvent, which may be, for example, chloroform. This is followed by a brine wash, drying of the enone-containing organic layer using anhydrous magnesuim sulfate, evaporation of the extraction solvent and drying of the resulting solid.

Step 3b:

In the next step of the present process, compound of formula (VII) is prepared by the reduction of compound of formula (VI), preferably by catalytic hydrogenation of that compound. Suitable catalysts include, for example, noble metal catalysts, which may be provided on a suitable support and may be chemically combined (e.g., platinum on carbon, palladium on carbon, palladium hydroxide on carbon, rhodium on carbon, platinum oxide, palladium diacetate, palladium dichloride, palladium tetrakis, rhodium diacetate and rhodium trichloride). Charcoal-supported 10% palladium is preferred. It is used in an amount sufficient to provide about 0.1 part palladium per part of compound (VI).

The reduction reaction is preferably carried out in the presence of an inert organic liquid medium, for example, an alcohol (e.g., ethanol), an ester (e.g., ethyl acetate), or an acid (e.g., acetic acid or formic acid). The solvent is preferably glacial acetic acid.

Suitable conditions for the reduction reaction in Step 3b include the addition or presence of, per mole of the compound of formula (VI) about 0.1-100 g of the catalyst employed (preferably about 22 g of 10% Pd on charcoal) and about 0.1-10 liters of an organic solvent (preferably about 2.3 liters of glacial acetic acid). The reaction may suitably be effected at, for example, about 1-10 atmospheres pressure, preferably about 7 atmospheres of hydrogen, and a temperature of about 25° C.-80° C., preferably 40° C.-55° C., and more preferably about 45° C. The reaction can be completed within about 4 hours under the preferred conditions.

The product of Step 3b, i.e., the compound of formula (VII), can be recovered in any suitable manner, preferably effected by filtering the reaction mixture through Celite diatomaceous earth to remove the catalyst, evaporating the solvent from the filtrate, dissolving the filtration residue in an organic solvent, preferably chloroform, washing the organic layer with water, removing the washed organic phase and evaporating solvent therefrom. The remaining solid residue is dissolved in an alcoholic solvent, preferably 2-propanol, under reflux until the solid has dissolved; at which point the mixture is cooled slowly, preferably to a temperature of 0° C.-5° C., at which point a solid precipitate begins to form. The mixture is filtered, the solid precipitate is collected and dried, thus providing the desired product. The recrystallization process may be repeated on the resulting filtrate in order to obtain a second crop of the desired product.

Step 3:

Following the completion of the reaction as monitored by HPLC analysis of the reaction mixture and prior to the extraction procedure as described above in Step 3a, recovery of the compound of formula (VI) can be satisfactorily omitted prior to initiation of Step 3b, which can proceed in situ in the reaction mixture of Step 3a.

The one-pot conversion of compound of formula (V) to the compound of formula (VII) via the in situ formation of compound of formula (VI) proceeds by contacting compound of formula (V) dispersed in an inert organic solvent with a pre-formed solution of a peroxy oxidation agent capable of introducing a beta-oriented hydroxyl group at the C-14 position as described above in Step 3a at a reduced temperature with stirring under an inert atmosphere of nitrogen until HPLC analysis detects <5% of the reactant of formula (V) (reaction time of about 2 hours), at which point activated charcoal may be added into the reaction mixture and stirred in order to quench any excess peroxide, followed by the addition of 10% palladium on charcoal and performing the catalytic reduction of compound of formula (VI) at an elevated temperature under an atmosphere of hydrogen gas as described above in Step 3b for a further 4 hours. At the end of the reaction, the bis-protected noroxymorphone of formula (VII) may be recovered from the reaction mixture in any suitable manner. Preferably, the recovery of compound of formula (VII) is effected using the same recovery procedure described in Step 3b above.

Therefore, it has been shown in the present invention that compound of formula (V) may be directly converted to compound of formula (VII) in a single-pot transformation via the in-situ formation of compound of formula (VI), thereby making the overall transformation pot- and atom-economical. This transformation is conducted using cheap, less toxic, highly stable reagents and can be performed under reactions parameters (such as reaction temperature and reaction pressure) that can be easily applied on an industrial scale.

Step 4:

In the final step of the present process, noroxymorphone of formula (I) is prepared from compound of formula (VII) by hydrolysis, preferably by contacting that compound with an acidic or basic hydrolysis catalyst preferably in the presence of water under hydrolytic conditions. Thereafter, noroxymorphone may be recovered by neutralizing the hydrolysis mixture with a neutralizing agent (for example, aqueous NH4OH), filtering the neutralized mixture, and washing and drying the filtrate.

Sulfuric acid is the preferred acidic catalyst and suitable basic hydrolysis catalysts include, for example, KOH, which may be employed as a solution thereof in ethanol, water, or diethylene glycol or the like.

Suitable conditions for the hydrolysis reaction using sulfuric acid include the addition of an amount of sulfuric acid (aqueous) corresponding to about 0.1-10 litres of 4.5 molar (M) aqueous sulfuric acid per mole of the compound of formula (VII). Preferably, about 4 litres of 4.5M aqueous sulfuric acid on the same basis are used. Hydrolysis may suitably be effected at, for example, atmospheric pressure and a temperature of about 70° C.-120° C., preferably 95° C.-105° C. under nitrogen atmosphere. The crude noroxymorphone thus obtained could be further purified by repeating the purification process described above.

According to the present invention, the process steps 1, 2a, 2b, 3a, 3b, and 4 can be performed in a batch reactor, or a continuous flow reactor, or a microwave reactor, or a combination thereof.

The following examples are provided to illustrate the present invention, but are not meant to be limiting. All parts and percentages given through this disclosure are by weight unless otherwise indicated. Unless otherwise indicated, the identity of the compounds prepared in each example was confirmed by mass spectroscopy, IR and NMR ($^1$H and $^{13}$C) and the reaction pressure in each example was approximately atmospheric.

EXAMPLES

Example 1: Step 1: Preparation of Compound of Formula (III) Using Acetone as a Solvent 3-O,N-bis-ethoxycarbonyl-normorphine (compound III with $R^1$ and $R^2$=ethoxycarbonyl)

To a stirred suspension of morphine (2.00 g, 7.0 mmol) and sodium bicarbonate (8.82 g, 105.0 mmol) in acetone (20 mL) was added ethyl chloroformate (6.00 mL, 63.0 mmol) in one portion and the resulting mixture was stirred at 40° C. for 6 hours. The reaction mixture was allowed to cool down to room temperature, i.e. about 20 to 25° C., filtered, and the solid residue washed with acetone (10 mL). The filtrate was collected and concentrated in vacuo, leaving 2.89 g of the title compound (99% of theory) having 98.25% purity as determined by HPLC analysis of the obtained title compound.

Example 2: Step 1: Preparation of Compound of Formula (III) Using Ethyl Acetate as a Solvent 3-O,N-bis-ethoxycarbonyl-normorphine (compound III with $R^1$ and $R^2$=ethoxycarbonyl)

To a stirred suspension of morphine (2.00 g, 7.0 mmol) and sodium bicarbonate (8.82 g, 105.0 mmol) in ethyl acetate (20 mL) was added ethyl chloroformate (6.00 mL, 63.0 mmol) in one portion and the resulting mixture was stirred at 75° C. for 6 hours. The reaction mixture was allowed to cool down to room temperature, i.e. about 20 to 25° C., filtered, and the solid residue washed with ethyl acetate (10 mL). The filtrate was collected and concentrated in vacuo, leaving 2.82 g of the title compound (97% of theory) having 98.66% purity as determined by HPLC analysis of the obtained title compound.

Example 3: Step 2a: Preparation of Compound of Formula (IV) Using Acetic Anhydride 3-O,N-bis-ethoxycarbonyl-normorphinone (compound IV with $R^1$ and $R^2$=ethoxycarbonyl)

To a stirred solution of 3-O,N-bis-ethoxycarbonyl-normorphine (2.00 g, 4.8 mmol) in acetic anhydride (4.54 mL, 48.0 mmol) was added dimethyl sulfoxide (1.71 mL, 24.0 mmol) in one portion under an inert atmosphere of nitrogen and the resulting mixture was stirred at 80° C. for 1.5 hours, at which point <2% of compound of formula (III) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 1.95 g of the title compound (98% of theory) having 99.10% purity as determined by HPLC analysis of the obtained title compound.

Example 4: Step 2a: Preparation of Compound of Formula (IV) Using Benzoic Anhydride 3-O,N-bis-ethoxycarbonyl-normorphinone (compound IV with $R^1$ and $R^2$=ethoxycarbonyl)

To a stirred solution of 3-O,N-bis-ethoxycarbonyl-normorphine (2.00 g, 4.8 mmol) in dimethyl sulfoxide (3.41 mL, 48.0 mmol) was added benzoic anhydride (10.9 g, 48.0 mmol) in one portion under an inert atmosphere of nitrogen and the resulting mixture was stirred at 80° C. for 1.5 hours, at which point <2% of compound of formula (III) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 1.78 g of the title compound (90% of theory) having 98.01% purity as determined by HPLC analysis of the obtained title compound.

Example 5: Step 2a: Preparation of Compound of Formula (IV) Using Glutaric Anhydride 3-O,N-bis-ethoxycarbonyl-normorphinone (compound IV with $R^1$ and $R^2$=ethoxycarbonyl)

To a stirred solution of 3-O,N-bis-ethoxycarbonyl-normorphine (2.00 g, 4.8 mmol) in dimethyl sulfoxide (3.41 mL, 48.0 mmol) was added glutaric anhydride (5.48 g, 48.0 mmol) in one portion under an inert atmosphere of nitrogen and the resulting mixture was stirred at 80° C. for 1.5 hours, at which point <2% of compound of formula (III) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 1.48 g of the title compound (75% of theory) having 96.59% purity as determined by HPLC analysis of the obtained title compound.

Example 6: Step 2a: Preparation of Compound of Formula (IV)

3-O-methoxy,N-ethoxycarbonyl-normorphinone (compound IV with $R^1$=methyl; and $R^2$=ethoxycarbonyl)

To a stirred solution of 3-O-methoxy,N-ethoxycarbonyl-normorphine (2.00 g, 5.6 mmol) in acetic anhydride (5.29 mL, 56.0 mmol) was added dimethyl sulfoxide (1.99 mL, 28.0 mmol) in one portion under an inert atmosphere of nitrogen and the resulting mixture was stirred at 80° C. for 1.5 hours, at which point <2% of compound of formula (III) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 1.91 g of the title compound (96% of theory) having 97.74% purity as determined by HPLC analysis of the obtained title compound.

Example 7: Step 2a: Preparation of Compound of Formula (IV)

3-O-acetyl,N-cyano-normorphinone (compound IV with $R^1$=acetyl; and $R^2$=cyano)

To a stirred solution of 3-O-acetyl,N-cyano-normorphine (2.00 g, 5.9 mmol) in acetic anhydride (5.58 mL, 59.0 mmol) was added dimethyl sulfoxide (2.10 mL, 29.5 mmol) in one portion under an inert atmosphere of nitrogen and the resulting mixture was stirred at 80° C. for 1.5 hours, at which point <2% of compound of formula (III) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 1.94 g of the title compound (98% of theory) having 99.08% purity as determined by HPLC analysis of the obtained title compound.

Example 8: Step 2a: Preparation of Compound of Formula (IV)

3-O-t-butyldimethylsilyl,N-cyano-normorphinone (compound IV with $R^1$=t-butyldimethylsilyl; and $R^2$=cyano)

To a stirred solution of 3-O-t-butyldimethylsilyl,N-cyano-normorphine (2.00 g, 4.4 mmol) in acetic anhydride (4.16 mL, 44.0 mmol) was added dimethyl sulfoxide (1.56 mL, 22.0 mmol) in one portion under an inert atmosphere of nitrogen and the resulting mixture was stirred at 80° C. for 1.5 hours, at which point <2% of compound of formula (III) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 1.94 g of the title compound (97% of theory) having 99.13% purity as determined by HPLC analysis of the obtained title compound.

Example 9: Step 2a: Preparation of Compound of Formula (IV)

morphinone (compound IV with $R^1$=hydrogen; and $R^2$=methyl)

To a stirred solution of morphine (2.00 g, 7.0 mmol) in acetic anhydride (6.62 mL, 70.0 mmol) was added dimethyl sulfoxide (2.13 mL, 30.0 mmol) in one portion under an inert atmosphere of nitrogen and the resulting mixture was stirred at 80° C. for 16 hours, at which point none of the title compound of formula (IV) was detected in the reaction mixture by HPLC analysis and the reaction was abandoned.

Example 10: Step 2b: Preparation of Compound of Formula (V) Using $Et_3N$ as Base 3-O,N-bis-ethoxycarbonyl-normorphinone dienol acetate (compound V with $R^1$ and $R^2$=ethoxycarbonyl; and $R^3$=acetyl)

To a stirred solution of 3-O,N-bis-ethoxycarbonyl-normorphinone (1.95 g, 4.7 mmol) in acetic anhydride (4.44 mL, 47.0 mmol) was added triethyl amine (1.64 mL, 11.8 mmol) in one portion under an inert atmosphere of nitrogen and the resulting mixture was stirred at 80° C. for 2.5 hours, at which point <2% of compound of formula (IV) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 2.13 g of the title compound (99% of theory) having 97.62% purity as determined by HPLC analysis of the obtained title compound.

Example 11: Step 2: One-Pot Preparation of Compound of Formula (V) Using NaOAc as Base 3-O,N-bis-ethoxycarbonyl-normorphinone dienol acetate (compound V with $R^1$ and $R^2$=ethoxycarbonyl; and $R^3$=acetyl)

To a stirred solution of 3-O,N-bis-ethoxycarbonyl-normorphine (2.00 g, 4.8 mmol) in acetic anhydride (11.34 mL, 120.0 mmol) was added dimethyl sulfoxide (3.41 mL, 48.0 mmol) in one portion under an inert atmosphere of nitrogen and the resulting mixture was stirred at 80° C. for 1.5 hours, at which point <2% of compound of formula (III) was detected in the reaction mixture by HPLC analysis. Sodium acetate (3.94 g, 48.0 mmol) was then added to the reaction mixture in one portion and was stirred at 80° C. for 3 hours. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 1.96 g of the title compound (90% of theory) having 94.34% purity as determined by HPLC analysis of the obtained title compound.

Example 12: Step 2: One-Pot Preparation of Compound of Formula (V) Using $Et_3N$ as Base 3-O,N-bis-ethoxycarbonyl-normorphinone dienol acetate (compound V with $R^1$ and $R^2$=ethoxycarbonyl; and $R^3$=acetyl)

To a stirred solution of 3-O,N-bis-ethoxycarbonyl-normorphine (2.00 g, 4.8 mmol) in acetic anhydride (11.34 mL, 120.0 mmol) was added dimethyl sulfoxide (3.41 mL, 48.0 mmol) in one portion under an inert atmosphere of nitrogen and the resulting mixture was stirred at 80° C. for 1.5 hours, at which point <2% of compound of formula (III) was detected in the reaction mixture by HPLC analysis. Triethylamine (6.69 mL, 48.0 mmol) was then added to the reaction mixture in one portion and stirred at 80° C. for 2.5 hours, at which point <2% of compound of formula (IV) was detected in the reaction mixture by HPLC analysis. The reaction mixture was allowed to cool down to room temperature, diluted with water (50 mL) and extracted with cyclopentylmethyl ether (3×50 mL). The combined organic extracts were washed with saturated aqueous sodium bicarbonate solution (3×25 mL), water (25 mL), dried over magnesium sulfate and concentrated in vacuo, leaving 2.04 g of the title compound (93% of theory) having 96.27% purity as determined by HPLC analysis of the obtained title compound.

Example 13a: Step 3a: Preparation of Compound of Formula (VI) Using Peracetic Acid 3-O,N-bis-ethoxycarbonyl-14-hydroxynormorphinone (compound VI with R1 and R2=ethoxycarbonyl)

To a stirred solution of 3-O,N-bis-ethoxycarbonyl-normorphinone dienol acetate (5.0 g, 11.0 mmol) in glacial acetic acid (15 mL) was added 50% aqueous H2O2 (8.10 mL, 114 mmol) in one portion under an inert atmosphere of nitrogen and the resulting mixture was stirred at 40° C. for 4 hours, at which point <2% of compound of formula (V) was detected in the reaction mixture by HPLC analysis. The reaction mixture was allowed to cool to room temperature, diluted with water (50 mL), and the pH was slowly adjusted to about 8 by addition of 2M aqueous ammonia (72 mL). The mixture was extracted with chloroform (3×60 mL). The combined organic extracts were washed with brine (75 mL), dried over magnesium sulfate and concentrated in vacuo, leaving 4.60 g of the title compound (98% of theory) having 92.31% purity as determined by HPLC analysis of the obtained title compound.

Example 13: Step 3a: Preparation of Compound of Formula (VI)

3-O,N-bis-ethoxycarbonyl-14-hydroxynormorphinone (compound VI with $R^1$ and $R^2$=ethoxycarbonyl)

A solution of 3-O,N-bis-ethoxycarbonyl-normorphinone dienol acetate (5.0 g, 11.0 mmol) in glacial acetic acid (30 mL) was stirred at 0° C. for 30 minutes under an inert atmosphere of nitrogen. In a separate flask, a solution of performic acid was prepared by stirring a mixture of formic acid (15.6 mL) and 50% aqueous $H_2O_2$ (3.13 mL) at 0° C. for 30 minutes under an inert atmosphere of nitrogen. The pre-formed solution of performic acid was added dropwise into the main reaction vessel containing the 3-O,N-bis-ethoxycarbonyl-normorphinone dienol acetate over 45 minutes via a syringe pump while maintaining the temperature at 0° C. and the resulting mixture was stirred for an additional 1.5 hours, at which point <2% of compound of formula (V) was detected in the reaction mixture by HPLC analysis. The reaction mixture was diluted with water (50 mL), and the pH was slowly adjusted to about 8 by addition of concentrated aqueous ammonia (72 mL). The mixture was allowed to warm to room temperature and extracted with chloroform (3×60 mL). The combined organic extracts were washed with brine (75 mL), dried over magnesium sulfate and concentrated in vacuo, leaving 4.62 g of the title compound (98% of theory) having 90.74% purity as determined by HPLC analysis of the obtained title compound.

Example 14: Step 3b: Preparation of Compound of Formula (VII)

3-O,N-bis-ethoxycarbonyl noroxymorphone (compound VII with $R^1$ and $R^2$=ethoxycarbonyl)

To a stirred solution of 3-O,N-bis-ethoxycarbonyl-14-hydroxynormorphinone (3.8 g, 8.8 mmol) in acetic acid (15 mL) was added 10% palladium on charcoal (190 mg) in an autoclave chamber and sealed. The reaction mixture was purged with a flow of nitrogen gas 3 times followed by hydrogen gas a further 3 times, and the resulting reaction mixture was stirred under an atmosphere of hydrogen at a temperature of 45° C. and a substantially constant reaction-chamber pressure of about 7 atmospheric pressure for 4 hours, at which point <2% of compound of formula (VI) was detected in the reaction mixture by HPLC analysis. The reaction mixture was cooled to 25° C. and the pressure within the reaction chamber was brought to 1 atmospheric pressure, the catalyst was removed by filtration through Celite diatomaceous earth and the filtrate was concentrated in vacuo. To the resulting residue was added chloroform (50 mL), and the organic phase was washed with water (10 mL), dried over magnesium sulfate and concentrated in vacuo. The remaining residue was dissolved in refluxing 2-propanol (15 mL), stirred for 20 minutes, and the mixture was slowly cooled to 0° C. at which point a precipitate began to form. The suspension was filtered, the precipitate collected and dried, leaving 3.34 g of the title compound (88% of theory) having 99.53% purity as determined by HPLC analysis of the obtained title compound. If required, the resulting filtrate could optionally be concentrated and the resulting residue subjected to the recrystallization process described above to obtain a second crop of the title compound.

Example 15: Step 3: Preparation of Compound of Formula (VII)

3-O,N-bis-ethoxycarbonyl noroxymorphone (compound VII with $R^1$ and $R^2$=ethoxycarbonyl)

A solution of 3-O,N-bis-ethoxycarbonyl-normorphinone dienol acetate (2.2 g, 4.8 mmol) in glacial acetic acid (13 mL) was stirred at 0° C. for 30 minutes under an inert atmosphere of nitrogen. In a separate flask, a solution of performic acid was prepared by stirring a mixture of formic acid (6.8 mL) and 50% aqueous $H_2O_2$ (1.37 mL) at 0° C. for 30 minutes under an inert atmosphere of nitrogen. The pre-formed solution of performic acid was added dropwise into the main reaction vessel containing the 3-O,N-bis-ethoxycarbonyl-normorphinone dienol acetate over 45 minutes via a syringe pump while maintaining the temperature at 0° C. and the resulting mixture was stirred for an additional 1.5 hours, at which point <2% of compound of formula (V) was detected in the reaction mixture by HPLC analysis. Activated charcoal (25 mg) was added into the reaction mixture and was stirred at a temperature of 25° C. for 30 minutes, followed by the addition of 10% palladium of charcoal (110 mg). The autoclave chamber was sealed and the reaction mixture purged with a flow of nitrogen gas for 10 minutes followed by a flow of hydrogen gas for a further 10 minutes, and the resulting reaction mixture was stirred under an atmosphere of hydrogen at a temperature of 45° C. and a substantially constant reaction-chamber pressure of about 7 atmospheric pressure for 4 hours, at which point <2% of compound of formula (VI) was detected in the reaction mixture by HPLC analysis. The reaction mixture was cooled to 25° C. and the pressure within the reaction chamber was reduced to 1 atmospheric pressure, the catalyst was removed by filtration through Celite diatomaceous earth and the filtrate was concentrated in vacuo. To the resulting residue was added chloroform (30 mL), and the organic phase was washed with water (10 mL), dried over magnesium sulfate and concentrated in vacuo. The remaining residue was dissolved in refluxing 2-propanol (10 mL), stirred for 20 minutes, and the mixture was slowly cooled to 0° C. at which point a precipitate began to form. The suspension was filtered, the precipitate collected and dried, leaving 1.90 g of the title compound (92% of theory) having 97.40% purity as determined by HPLC analysis of the obtained title compound. If required, the resulting filtrate could optionally be concentrated and the resulting residue subjected to the recrystallization process described above to obtain a second crop of the title compound.

Example 16: Step 4: Preparation of Compound of Formula (I)

Noroxymorphone (compound I)

A solution of 3-O,N-bis-ethoxycarbonyl noroxymorphone (7.00 g, 16.2 mmol) in 4.5M aqueous $H_2SO_4$ (40 mL) was stirred at 100° C. for 17 hours under an inert atmosphere of nitrogen, at which point <2% of compound of formula (VII) was detected in the reaction mixture by HPLC analysis. The reaction mixture was allowed to cool down to room temperature (25° C.), and the pH was slowly adjusted to about 9 by addition of concentrated aqueous ammonia (30 mL) at which point a solid precipitate began to form. The precipitate was filtered, collected, and dried, leaving 4.56 g of the title compound (98% of theory) having 95.54% purity as determined by HPLC analysis of the obtained title compound. Crude noroxymorphone of formula (I) thus formed could optionally be further purified as described below.

To a stirred solution of crude noroxymorphone (4.56 g, 15.9 mmol) in water (42 mL) was added 37% aqueous HCl (5.2 mL). The solution was stirred at 90° C. for 15 minutes under an inert atmosphere of nitrogen. The solution was cooled to room temperature and filtered. The pH of the resulting filtrate was adjusted to about 9 by the addition of concentrated aqueous ammonia (10 mL) at which point a solid precipitate began to form. The precipitate was filtered, collected, and dried, leaving 4.24 g of the title compound (91% of theory) having 98.82% purity as determined by HPLC analysis of the obtained title compound.

We claim:

1. A process for preparing noroxymorphone from morphine comprising:

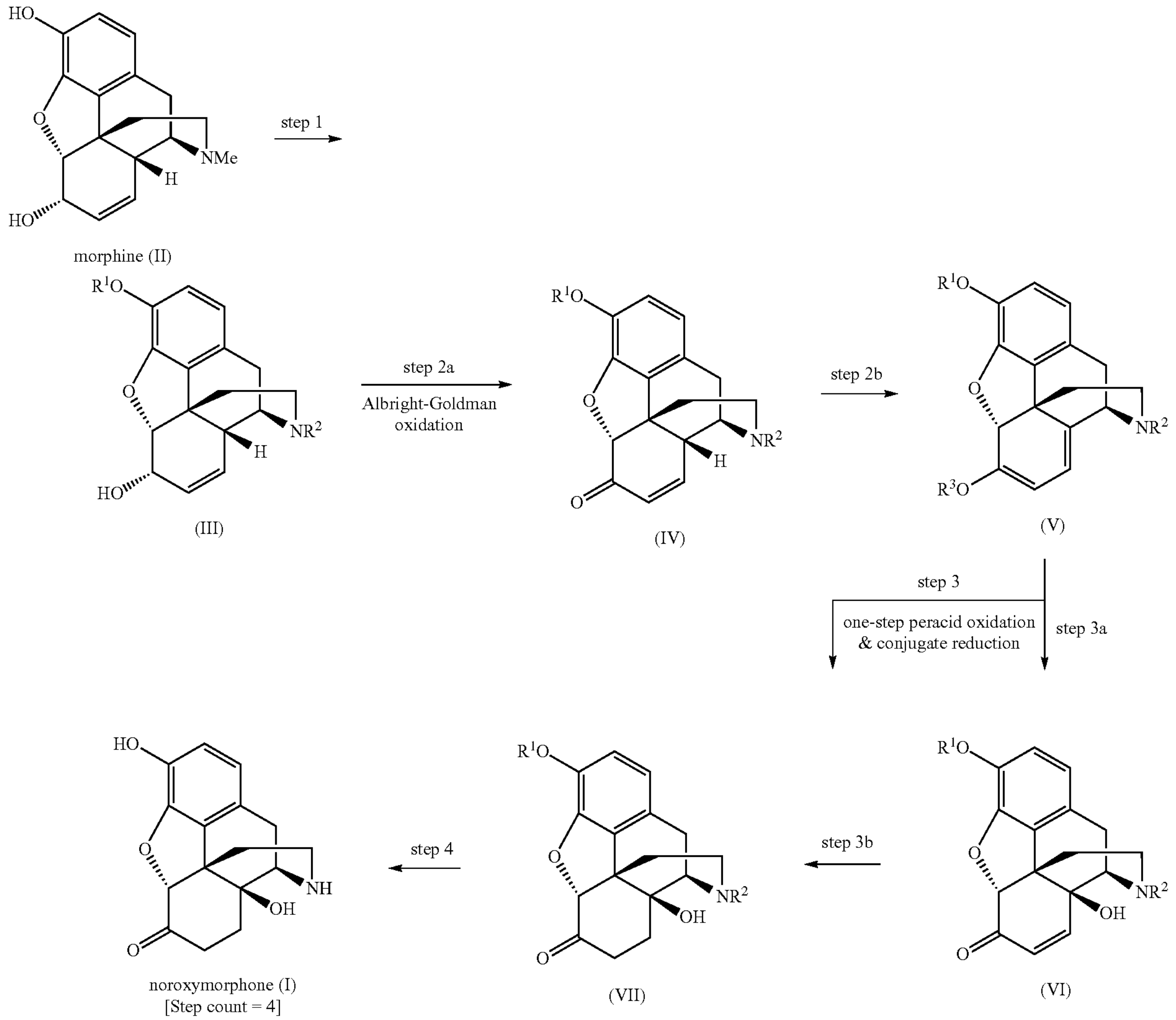

morphine (II)

(III)

(IV)

(V)

(VI)

(VII)

noroxymorphone (I)
[Step count = 4]

1) reacting morphine of formula (II) to obtain a compound of formula (III);

2a) oxidizing the compound of formula (III) with an oxidizing agent to obtain a compound of formula (IV);

2b) acylating the compound of formula (IV) with an acylation agent to obtain a compound of formula (V);

3a) subjecting the compound of formula (V) to peroxy oxidation to obtain a compound of formula (VI);

3b) reducing the compound of formula (VI) to obtain a compound of formula (VII); and 4) hydrolyzing the compound of formula (VII) to obtain noroxymorphone of formula (I);

wherein $R^1$ and $R^2$ independently are a substituted or unsubstituted alkyl group with 1 to 20 carbon atoms, or a substituted or unsubstituted aryl group, or a substituted or unsubstituted alkylaryl group with 1 to 20 carbon atoms, or a substituted or unsubstituted alkenyl group having 2 to 20 carbon atoms, or a substituted or unsubstituted alkoxycarbonyl group with 1 to 20 carbon atoms in the alkyl residue, or a substituted or unsubstituted aryloxycarbonyl group or a substituted or unsubstituted alkylaryloxycarbonyl group with 1 to 20 carbon atoms in the alkyl residue, or a cyanide group, or a silyl group of formula $Si(R^4)_3$, wherein the groups $R^4$ can be the same or different and are each selected from substituted or unsubstituted alkyl groups having 1 to 6 carbon atoms and substituted or unsubstituted aryl groups, respectively, and wherein $R^3$ is a substituted or unsubstituted alkylcarbonyl group having 1 to 20 carbon atoms in the alkyl residue, or a substituted or unsubstituted alkylarylcarbonyl group having 1 to 20 carbon atoms in the alkyl residue, or a substituted or unsubstituted arylcarbonyl group, or a substituted or unsubstituted alkenylcarbonyl group having 2 to 20 carbon atoms, respectively;

wherein step 2a is conducted by oxidizing the compound of formula III with an acyclic or cyclic organic acid anhydride and a dialkyl sulfoxide at or above room temperature;

wherein step 2a and step 2b are optionally combined into a one-pot single-step transformation, and wherein step 3a and step 3b are optionally combined into a one-pot single-step transformation.

2. A process for preparing noroxymorphone from morphine comprising:

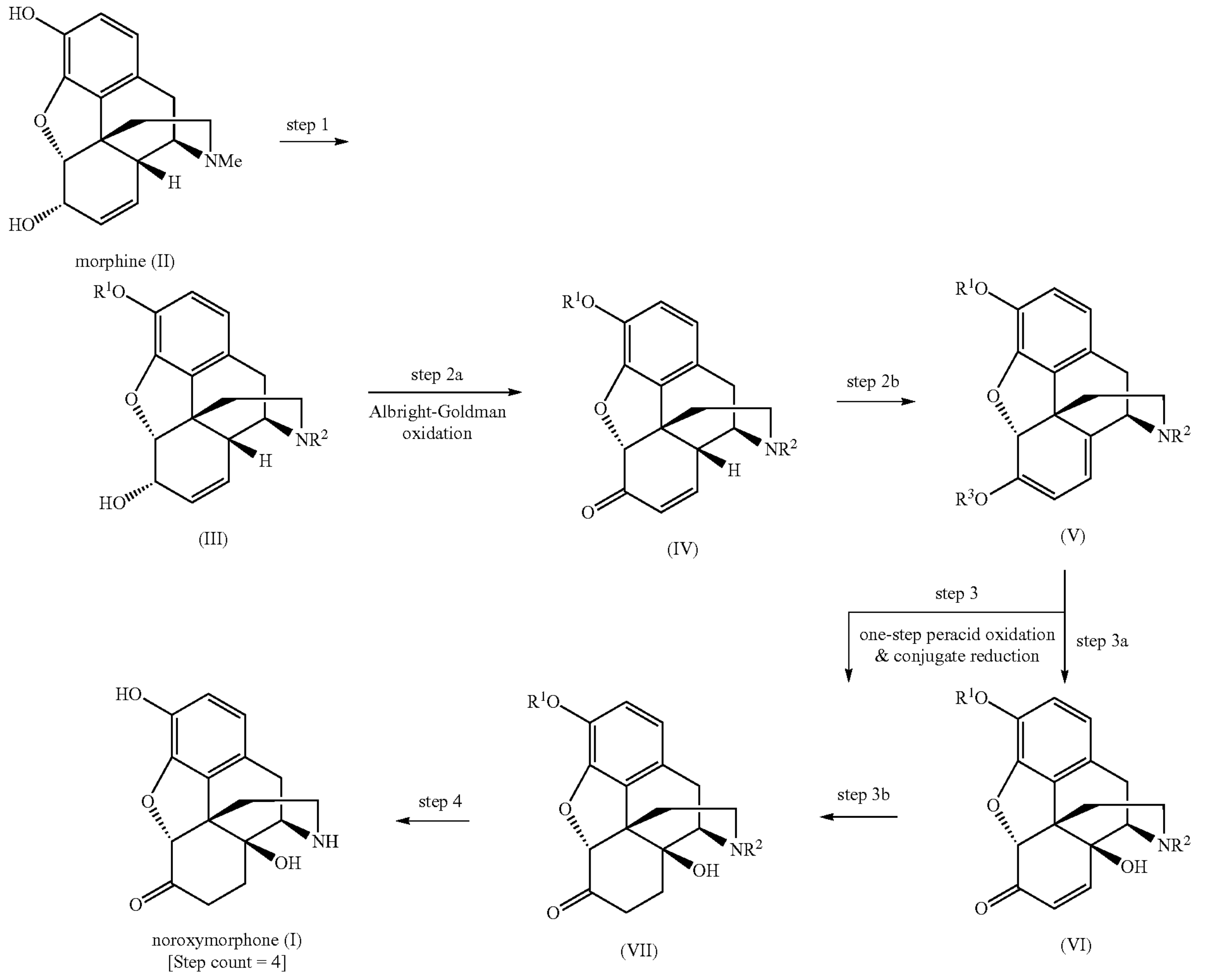

1) reacting morphine of formula (II) to obtain a compound of formula (III);

2) in a first one-pot single step transformation, oxidizing the compound of formula (III) with an Albright-Goldman oxidizing agent using Albright-Goldman oxidation conditions to obtain a compound of formula (IV), and acylating the compound of formula (IV) with an acylation agent to obtain a compound of formula (V);

3) in a second one-pot single step transformation, subjecting the compound of formula (V) to peroxy oxidation to obtain a compound of formula (VI), and reducing the compound of formula (VI) to obtain a compound of formula (VII); and 4) hydrolyzing the compound of formula (VII) to obtain noroxymorphone of formula (I);

wherein $R^1$ and $R^2$ independently are a substituted or unsubstituted alkyl group with 1 to 20 carbon atoms, or a substituted or unsubstituted aryl group, or a substituted or unsubstituted alkylaryl group with 1 to 20 carbon atoms, or a substituted or unsubstituted alkenyl group having 2 to 20 carbon atoms, or a substituted or unsubstituted alkoxycarbonyl group with 1 to 20 carbon atoms in the alkyl residue, or a substituted or unsubstituted aryloxycarbonyl group or a substituted or unsubstituted alkylaryloxycarbonyl group with 1 to 20 carbon atoms in the alkyl residue, or a cyanide group, or a silyl group of formula $Si(R^4)_3$, wherein the groups $R^4$ can be the same or different and are each selected from substituted or unsubstituted alkyl groups having 1 to 6 carbon atoms and substituted or unsubstituted aryl groups, respectively, and wherein $R^3$ is a substituted or unsubstituted alkylcarbonyl group having 1 to 20 carbon atoms in the alkyl residue, or a substituted or unsubstituted alkylarylcarbonyl group having 1 to 20 carbon atoms in the alkyl residue, or a substituted or unsubstituted arylcarbonyl group, or a substituted or unsubstituted alkenylcarbonyl group having 2 to 20 carbon atoms, respectively.

3. The process according to claim 2, wherein the Albright-Goldman oxidizing agent comprises dimethyl sulfoxide (DMSO) and an acyclic or cyclic organic acid anhydride.

4. The process according to claim 3, wherein said acid anhydride is selected from the group consisting of acetic anhydride, benzoic anhydride, propionic anhydride, butanoic anhydride, pentanoic anhydride, hexanoic anhydride, isobutyric anhydride, isovaleric anhydride, acrylic anhydride, methacrylic anhydride, angelic anhydride, crotonic anhydride, pivalic anhydride, trifluoroacetic anhydride, difluoroacetic anhydride, monofluoroacetic anhydride, pentafluoropropionic anhydride, chloroacetic anhydride, succinic anhydride, maleic anhydride, glutaric anhydride, adipic anhydride, 3-methylglutaric anhydride, 3,3-dimethylglutaric anhydride, hexafluoroglutaric anhydride, phthalic anhydride, and homophthalic anhydride.

5. The process according to claim 1, wherein said acid anhydride is selected from the group consisting of acetic anhydride, benzoic anhydride, propionic anhydride, butanoic anhydride, pentanoic anhydride, hexanoic anhydride, isobutyric anhydride, isovaleric anhydride, acrylic anhydride, methacrylic anhydride, angelic anhydride, crotonic anhydride, pivalic anhydride, trifluoroacetic anhydride, difluoroacetic anhydride, monofluoroacetic anhydride, pentafluoropropionic anhydride, chloroacetic anhydride, succinic anhydride, maleic anhydride, glutaric anhydride, adipic anhydride, 3-methylglutaric anhydride, 3,3-dimethylglutaric anhydride, hexafluoroglutaric anhydride, phthalic anhydride, and homophthalic anhydride.

6. The process according to claim 1, wherein, the oxidation reaction in step 2a is carried out at atmospheric pressure and a temperature of about room temperature to 120° C.

7. The process according to claim 6, wherein, the oxidation reaction is conducted at 55° C. to 65° C.

8. The process according to claim 3, wherein the acylation agent is acetic anhydride.

9. The process according to claim 1, wherein, the acylation in step 2b is conducted in presence of sodium acetate or triethylamine.

10. The process according to claim 1, wherein step 3a is performed with pre-formed performic acid under substantially anhydrous conditions in glacial acetic acid at a temperature of −10° C. to 100° C.

11. The process according to claim 10, wherein, the performic acid is prepared by treating formic acid with no less than 30% hydrogen peroxide.

12. The process according to claim 1, wherein step 3a is performed with peracetic acid, which may be preformed or generated in situ, under substantially anhydrous conditions in glacial acetic acid at a temperature of −10° C. to 100° C.

13. The process according to claim 1, wherein, the reducing agent used in step 3b) is 10% palladium on carbon.

14. The process according to claim 13, wherein, the reduction is conducted at a temperature range of 25° C. to 80° C. in glacial acetic acid.

15. The process according to claim 1, wherein, the hydrolysis in step 4 is conducted in the presence of an acidic hydrolysis catalyst such as sulfuric acid or a basic hydrolysis catalyst such as potassium hydroxide.

16. The process according to claim 1, wherein, the process steps 2a, 2b, 3a and 3b are conducted in different pots.

17. The process according to claim 1, wherein, the process steps 1, 2a, 2b, 3a, 3b, and 4 are performed in a batch reactor, or a continuous flow reactor, or a microwave reactor, or a combination thereof.

18. The process according to claim 1, wherein, the $R^1$ and $R^2$ is an ethoxycarbonyl group and $R^3$ is an acetyl group.

19. The process according to claim 1, wherein:

step 2a and step 2b are combined into a one-pot single-step transformation, and/or step 3a and step 3b are combined into a one-pot single-step transformation.

* * * * *